United States Patent [19]

Strein

[11] Patent Number: 5,366,965
[45] Date of Patent: Nov. 22, 1994

[54] REGIMEN FOR TREATMENT OR PROPHYLAXIS OF OSTEOPOROSIS

[75] Inventor: Klaus Strein, Hemsbach, Germany

[73] Assignee: Boehringer Mannheim GmbH, Mannheim, Germany

[21] Appl. No.: 11,008

[22] Filed: Jan. 29, 1993

[51] Int. Cl.$^5$ ............................................. A61K 31/66
[52] U.S. Cl. .................................. 514/102; 514/107; 514/108
[58] Field of Search ............... 514/102, 107, 108, 141, 514/86, 89

[56] References Cited

U.S. PATENT DOCUMENTS

| | | | |
|---|---|---|---|
| 4,761,406 | 8/1988 | Flora et al. | 514/86 |
| 4,812,304 | 3/1989 | Anderson | 514/141 |
| 4,812,311 | 3/1989 | Uchtman | 514/141 |
| 5,153,183 | 10/1992 | Kawbe et al. | 514/76 |
| 5,196,409 | 3/1993 | Breuer et al. | 514/108 |

*Primary Examiner*—Marianne M. Cintins
*Assistant Examiner*—T. J. Criares
*Attorney, Agent, or Firm*—Nikaido Marmelstein Murray & Oram

[57] ABSTRACT

Methods for treating or preventing osteoporosis, including regimens for intermittent dosing of bone resorption inhibiting polyphosphonate compound or a pharmaceutically acceptable salt or ester of any such compound.

12 Claims, 3 Drawing Sheets

Fig.2

| GROUP | 2 WEEKS | 4 WEEKS OFF | 2 WEEKS | 4 WEEKS OFF | 2 WEEKS | 4 WEEKS OFF |
|---|---|---|---|---|---|---|
| D OR DS | 14 TIMES 0.003 mg/kg | | 14 TIMES 0.003 mg/kg | | 14 TIMES 0.003 mg/kg | |
| GROUP | 2 WEEKS | 4 WEEKS OFF | 2 WEEKS | 4 WEEKS OFF | 2 WEEKS | 4 WEEKS OFF |
| E OR ES | 7 TIMES 0.006 mg/kg | | 7 TIMES 0.006 mg/kg | | 7 TIMES 0.006 mg/kg | |
| GROUP | 2 WEEKS | 4 WEEKS OFF | 2 WEEKS | 4 WEEKS OFF | 2 WEEKS | 4 WEEKS OFF |
| F OR FS | 2 TIMES 0.021 mg/kg | | 2 TIMES 0.021 mg/kg | | 2 TIMES 0.021 mg/kg | |

REGIMEN FOR TREATMENT OR PROPHYLAXIS OF OSTEOPOROSIS

TECHNICAL FIELD

The present invention relates to methods for treating or preventing osteoporosis. More particularly, the present invention relates to well-defined regimens for intermittent dosing of bone resorption inhibiting polyphosphonate compounds. The present invention also relates to a kit to be used by patients for treatment in accordance with the treatment regimen.

BACKGROUND OF THE INVENTION

Post menopausal osteoporosis is by far the most common form of osteoporosis. Various therapies have been approved in the United States, including the administration of oral estrogen, sodium fluoride, and, on an experimental basis, intranasal calcitonin. However, the widespread use of these agents has been limited by various factors, including expense, safety and lack of proved efficacy. A search continues in the art for an inexpensive, safe and effective treatment for osteoporosis.

Organic bisphosphonate compounds have been found to inhibit bone resorption which is mediated by osteoclasts. The earliest publication describing the administration of diphosphonates for treatment of osteoporosis was in 1979 when Frost described the "Treatment of osteoporosis by manipulation of coherent bone cell populations." Frost continued a series of publications (Frost, "The ADFR Concept and Monitoring It:" in *Bone Histomorphometry* 1980, 317–321; Frost, "The Evolution of Osteoporosis Therapy" in *Orthopedic Clinics of North America*, 12, 603–610, 1981; Frost, "Coherence Treatment of Osteoporosis," *Orthopedic Clinics of North America*, Vol. 12, 649–669, 1981; and others). This coherence concept has been modified by several other authors. In principle, it consists of a stimulation of bone turnover with phosphorus or parathyroid hormone, followed by blocking the resorption with intermittent therapy of blocking agents such as calcitonin or diphosphonates. This therapy, although theoretically very attractive, did not find widespread application because of the difficulty in determining a correct dose for an individual patient and the correct period of time required for stimulation and suppression of individual bone remodelling sites (without exerting an effect on formation). It appears that somewhere between three days and three weeks, most resorption sites should be suppressed. However, no exact information is available anywhere to unequivocally prove this hypothesis.

Since the work by Frost in 1979, many have conceived of different treatment regimens using different compounds and modes of administration. U.S. Pat. No. 4,761,406 to Flora et. al. represents one such example, and is an example of the well-known coherence therapy (except that the stimulation step is apparently omitted, with no apparent advantage to omitting that step). Flora '406 discloses and claims a treatment regimen which employs compounds (polyphosphonates) known in the prior art for treatment of osteoporosis. According to the regimen disclosed in U.S. Pat. No. 4,761,406, at least two cycles are performed, each cycle comprising a daily administration period, during which the polyphosphonate is administered every day, and a rest period.

The bisphosphonate etidronate has been used in animal and clinical trials in the treatment of osteoporosis in various regimes, including continuous therapy, in intermittent cyclic therapy or DFR (Depress, Free, Repeat), or in combination with other agents in an intermittent cyclic therapy known as ADFR (Activate, Depress, Free, Repeat) (see the Frost references mentioned above).

U.S. Pat. Nos. 4,812,304, 4,812,311 and 4,822,609 disclose the use of ethene-1-hydroxy-1, 1-diphosphonic acid or salts or esters thereof in the ADFR treatment. The treatment comprises one or more cycles, wherein each cycle includes a bone activating period of 1 to 5 days during which a bone activating amount of a bone cell activating compound is administered daily. That step is followed by a bone resorption inhibition period of about 10 to 20 days, during which ethane-1-hydroxy-1,1-diphosphonic acid or salt or ester thereof is administered daily in a relatively low amount, followed by a rest period of 30 to 180 days, during which the patient receives neither a bone cell activating compound nor a bone resorption inhibiting polyphosphonate. Other bone resorption inhibiting polyphosphonates are disclosed but not claimed in these patents.

U.S. Pat. No. 4,761,406 discloses basically the same process as described in the patents mentioned in the above paragraph, except that the bone cell activating compound administration step is eliminated. Thus, a treatment regime is suggested involving administering a bone resorption inhibiting polyphosphonate on a daily basis and in a limited amount, followed by a rest period of about 50 to 120 days, with such a treatment regime being repeated at least twice. The patent claims an increase in bone mass results, which is also a result disclosed in U.S. Pat. Nos. 4,812,304, 4,812,311 and 4,822,609.

Treatment for osteoporosis typically requires extended, sometimes chronic, treatment, and patient compliance is a major problem. Those who suffer from osteoporosis would benefit significantly from a new treatment regime which is effective, is easy to administer and/or requires fewer administrations, and avoids or minimizes side effects such as gastrointestinal problems (e.g., as caused by bisphosphonates such as clodronate and pamidronate, when administered orally). Such persons would also benefit from a new treatment regime which can be administered by a wider variety of modes.

SUMMARY OF THIS INVENTION

The present invention provides such a new treatment regime. The present invention stems from an experiment conducted by the present inventors, which experiment had a surprising outcome. In that experiment, different groups of ovariectomized rats were administered sodium salt of 1-hydroxy-3-(N-methyl-N-pentylamino)-propane-1,1-diphosponic acid (BM 21.0955) in the indicated amount (calculated as free acid) in physiological saline solvent:

(1) administered 1 $\mu$g/kg BM 21.0955 daily for 18 weeks.

(2) 3 $\mu$g/kg BM 21.0955 administered daily for 14 days, then given a 4 week drug-free period, then administered 3 $\mu$g/kg BM 21.0955 daily for another 14 days, then given another 4 week drugfree period, then administered 3 $\mu$g/kg BM 21.0955 daily for another 14 days, and then given another 4 week drug-free period.

(3) the same treatment as in (2), above, except that during the 14 day treatment periods, BM 21.0955 was administered only every second day, in a dose of 6 $\mu$g/kg.

(4) the same treatment as in (2), above, except that during the 14 day treatment periods, on the first day, 21 μg/kg were administered and on the eighth day, another 21 μg/kg were administered.

Despite the intermittent administration employed in (3) and (4), in each group of rats, bone loss induced by ovariectomy was totally prevented.

The present invention thus provides methods for the treatment and/or prophylaxis of osteoporosis, which methods comprise at least two cycles, each cycle comprising an inhibiting period followed by a rest period. The inhibiting periods last for 4–90 days, and comprise at least two intermittent periods. The intermittent periods may be of the same or of different duration, and last for 2 to about 14 days. The drug is administered on only one day of each intermittent period. The rest periods last for 20–120 days.

In accordance with the present invention, the drug comprises a bone resorption inhibiting polyphosphonate (or a physiologically acceptable salt or ester thereof), preferably a diphosphonate (or a physiologically acceptable salt or ester thereof), most preferably a compound of the formula:

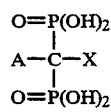

formula 1 wherein
A is a hydrocarbyl residue which may include X;
X is H, OH, Cl or part of A.

Preferred modes of administration in accordance with the present invention include oral, intravenous and subcutaneous.

A modification of the present invention further includes an activation period conducted prior to the first inhibiting period. Any suitable bone cell activating compound may be administered during such activation period. A suitable activation period comprises daily administration of a bone cell activating effective amount of a bone cell activating compound for 1–30 days. The desirability of using an activation period depends, among other things, on the turnover rate of the patient being treated. That is, an activating period is especially useful for low turnover patients.

The present invention also provides kits for use in administering treatment in accordance with the methods according to the present invention.

BRIEF DESCRIPTION OF THE DRAWINGS FIGURES

FIG. 2 is a chart of dose regimens employed in Example 2.

DETAILED DESCRIPTION OF THE PREFERRED EMBODIMENTS

Figure 1:
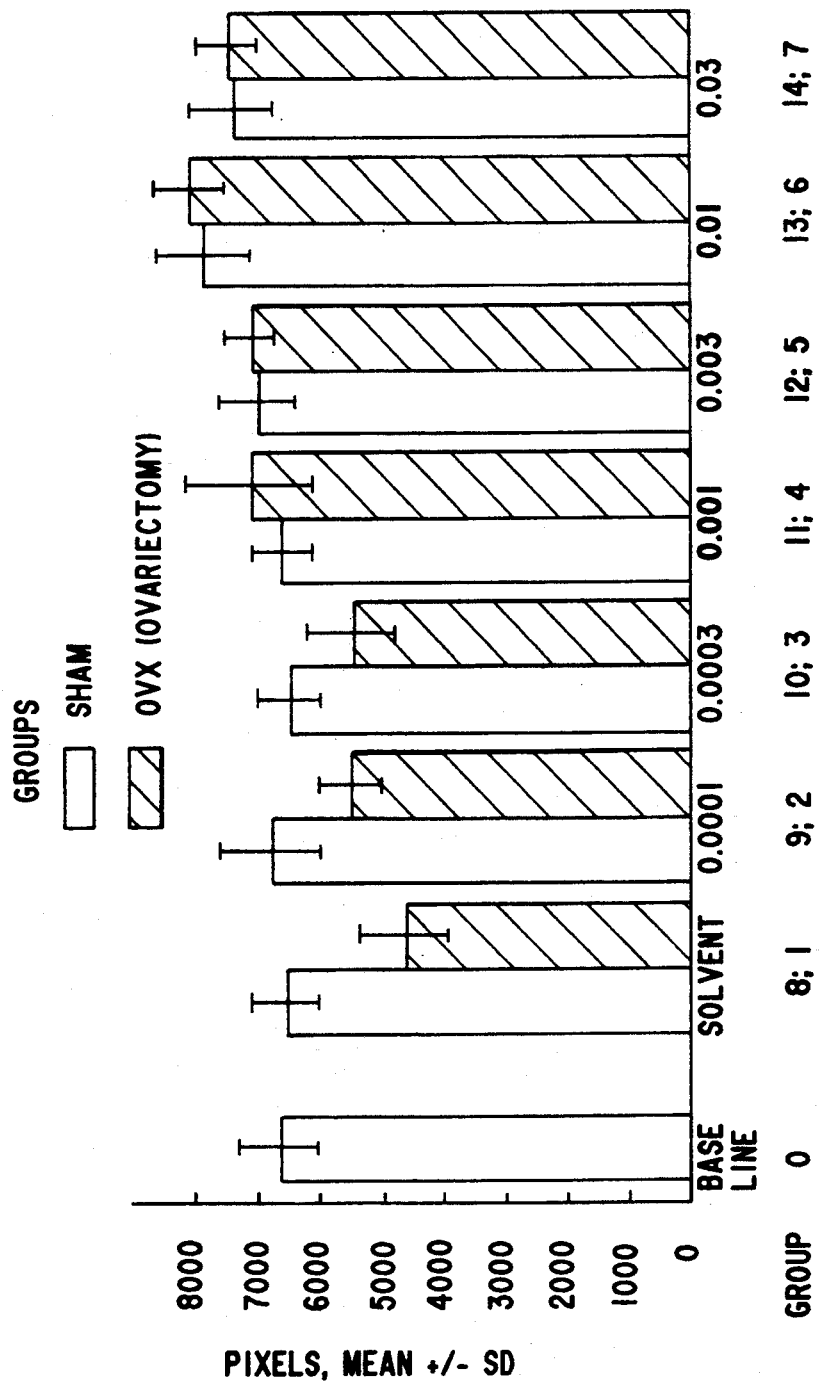
FIG. 1 is a plot of x-ray densities from tests conducted in Example 1.

In accordance with the present invention, there are provided methods which comprise at least two cycles, each cycle comprising an inhibiting period followed by a rest period. The inhibiting periods preferably last for 4–90 days, more preferably 7–50 days, more preferably about 7–21 days, most preferably about 14 days, and comprise at least two intermittent periods. The intermittent periods may be of the same or of different duration, and preferably last for 2 to about 14 days, more preferably 2–10 days, more preferably about 5–10 days, most preferably about 7 days. The drug is administered on only one day of each intermittent period. Representative suitable inhibiting periods are as follow:

2 or 3 intermittent periods, each 7 days long;
2 to 5 intermittent periods, each 5–10 days long;
2 to 10 intermittent periods, each 4–14 days long.

The rest periods preferably last for 20–120 days, more preferably 50–100 days, more preferably about 60–84 days, most preferably about 75–80 days.

The cycles preferably last for 24–210 days, more preferably 57–150 days, more preferably about 67–105 days, most preferably about 90 days (90 days is approximately the same as a typical bone turnover cycle in an adult human). For example, a representative suitable cycle might include a 14 day inhibiting period (two 7-day intermittent periods) and a 2½ month rest period.

In accordance with the present invention, the drug may comprise any suitable bone resorption inhibiting polyphosphonate, or physiologically acceptable salt or ester thereof. Preferred drugs include the diphosphonates (and physiologically acceptable salts and esters thereof), most preferably a compound of formula 1, above (and physiologically acceptable salts and esters thereof). Any of the polyphosphonate compounds disclosed in U.S. Pat. Nos. 4,927,814, 4,812,304, 4,812,311 and 4,822,609, the entire disclosures of which are hereby incorporated by reference, are suitable. Preferred specific examples of diphosphonates which are suitable for use according to the present invention include:

1-hydroxyethane-1,1-diphosphonic acid (etidronate);
4-amino-1-hydroxybutane-1,1-diphosphonic acid (alendronate);
3-amino-1-hydroxypropane-1,1-diphosphonic acid (pamidronate);
(4-chlorphenyl)thiomethane-1,1-diphosphonic acid (tiludronate);
1-hydroxy-2-(3-pyridyl)ethane-1,1-diphosphonic acid (risedronate);
1-hydroxy-1-(1-imidazolyl)ethane-1,1-diphosphonic acid (CGP-42446 - disclosed in European Patent Publication EP-A-275 821);
1,1-dichlormethane-1,1-diphosphonic acid (clodronate);
cycloheptylaminomethane-1,1-diphosphonic acid (YM175);
3-dimethylamino-1-hydroxypropane-1,1-diphosphonic acid (dimethyl-APD);
1-hydroxy-3-(1-pyrrolidinyl) propane-1,1-diphosphonic acid (EB 1053);
1-hydroxy-2-(2-pyridyl)ethane-1,1-diphosphonic acid;
1-hydroxy-3-(N-methyl-N-pentyl-amino)-propane-1,1-diphosphonic acid (BM 21.0955); and
1-hydroxy-3-(1-iminoethyl)aminopropane-1,1-diphosphonic acid (disclosed in West German Patent Publication DE-A-42 23 940.0, filed Jul. 21, 1992).

Preferred modes of administration of polyphosphonates in accordance with the present invention include oral, intravenous and subcutaneous. A suitable subcutaneous treatment regime could comprise only several injections over a several month period, e.g., injections in 14 days (for example, an injection on day 1, no injection on days 2–7, an injection on day 8 and no injection on days 9–14), followed by a rest period of, e.g., 2 months, followed again by two injections in 14 days (thus consisting of four injections over a 3 month period). Oral administration typically provides only about 1–3% bioavailability (bioavailability varies from one patient to another). Much higher bioavailability is provided by subcutaneous and intravenous administration according to the present invention.

Suitable polyphosphonate dosages depend on many factors, e.g., the patient's weight, the mode of administration, the type and degree of osteoporosis, etc. Suitable dosages can be determined by those skilled in the art without undue experimentation. Representative suitable dosages for various polyphosphonates are set forth in U.S. Pat. Nos. 4,812,304, 4,812,311 and 4,822,609, incorporated herein by reference.

Suitable carriers for the polyphosphonate depend on various factors, including the mode of administration, and are well known by those of skill in this art.

The total treatment time (i.e., the number of cycles for treatment) for the method of treatment of the present invention will vary from patient to patient based on sound medical judgment and factors particular to the patient being treated such as, for example, the extent of bone loss prior to starting treatment, the age and physical condition of the patient, and whether the goal of the treatment is to prevent bone loss or build bone mass. For example, if a certain percent increase in bone mass is desired from the method of treatment of the present invention, the total treatment time is as long as it takes to obtain this goal as determined through bone measurement. Those skilled in the art know the factors to be considered, and can easily determine the total treatment time based on these factors on a patient by patient basis. By "patient in need of osteoporosis treatment or prophylaxis" is meant a subject diagnosed as suffering from one or more of the various forms of osteoporosis, or a subject belonging to a group known to have a significantly higher than average chance of developing osteoporosis, e.g., postmenopausal women, men over age 65, and persons being treated with drugs known to cause osteoporosis as a side effect (such as adrenocorticoids).

By "rest period" as used herein is meant a period of time during which the patient is not given a bone resorption inhibiting polyphosphonate, nor is the patient subjected to a bone cell activating amount of a bone cell activating compound or other conditions which would result in significant activation or inhibition of new bone remodelling units. However, this is not to say that no chemicals may be administered to the patient during the rest period. Nutrient supplements like calcium, vitamin D (to be distinguished from bone cell activating amounts of bone cell activating metabolites of vitamin D) iron, niacin, vitamin C and other vitamin or mineral supplements (which do not significantly affect the BRUs) can beneficially be administered during the rest period. Certain medications which do not significantly affect the BRUs, such as, e.g., calcitonin and adrenocorticosteroids, are not to be administered during the rest period. A placebo (e.g., a sugar pill) may also be administered during the intermittent periods and/or the rest periods to assist in following the regimen of the present invention, especially if no daily supplement is being given during the rest period.

By "pharmaceutically acceptable salts and esters" as used herein is meant hydrolyzable esters and salts of the diphosphonate compounds which have the same general pharmacological properties as the acid form from which they are derived, and which are acceptable from a toxicity viewpoint. Pharmaceutically acceptable salts include alkali metal (e.g., sodium and potassium), alkaline earth metal (e.g., calcium and magnesium), and ammonium and low molecular weight substituted ammonium (e.g., mono-, di- and triethanolamine) salts.

As mentioned above, a modification of the present invention further includes an activation period conducted prior to the first inhibiting period. Any suitable bone cell activating compound may be administered during such activation period. The phrase "bone cell activating compound" as used herein, means any compound which increases the rate of activation of new bone turnover packets in adults. Suitable bone cell activating compounds (and bone cell activating amounts) are disclosed in U.S. Pat. No. 4,761,406, the entire disclosure of which is hereby incorporated by reference. A suitable activation period comprises daily administration of a bone cell activating effective amount of a bone cell activating compound for 1–30 days.

The methods according to the present invention are applicable to the treatment of all kinds of mammals, particularly humans.

The present invention further relates to a kit for conveniently and effectively implementing methods of treatment in accordance with this invention. Such a kit preferably includes a number of unit dosages which makes convenient the correct administration of the dosages in a treatment regime according to this invention, as disclosed above. For example, in a treatment regime comprising cycles each including inhibiting periods which consist of 3 intermittent periods, each seven days long, it would be suitable to group dosages in sets of three, one for each of the three intermittent periods during each inhibiting period, and to indicate beside each dosage the date on which that dosage should be administered. Alternatively or additionally, it would be suitable to include a number of placebo dosages (preferably in a form similar to the polyphosphonate dosages and comprising an inert material or, e.g., a nutrient supplement) equal to the number of days for which polyphosphonate is not administered.

One specific embodiment of the invention comprises a card having the components of the treatment regimen in the order of their intended use. An example of such a card is a "blister pack". Blister packs are well known in the packaging industry, and are being widely used for packaging pharmaceutical unit dosage forms. Blister packs generally comprise a sheet of relatively stiff material, covered with a foil of a plastic material, preferably transparent. During the packaging process, recesses are formed in the plastic foil. The recesses have a size and shape which accommodate the dosages. Next, the dosages (and placebo articles, when present) are placed in the recesses, and the sheet of stiff material is sealed against the plastic foil, sealing the dosages inside. As is well known, it is desirable to provide a memory aid on the card, e.g., in the form of numbers adjacent to the dosages, which numbers correspond to the days in the regimen in which the dosages should be administered, e.g., the date.

Other types of packaging will be readily apparent to those skilled in the art, e.g., single dosage dispensers, etc.

The present invention provides numerous advantages. For example, the number, frequency and/or dosages of administrations can be significantly reduced. In addition, the present invention does not cause gastrointestinal problems or fever to the extent seen with patients subjected to other osteoporosis treatment regimes. Also, the present invention makes it possible to administer treatment subcutaneously or intravenously, without causing skin problems, as would be experienced with other treatment regimes, in which dosages would have to be too large for such administrations. The present invention will increase patient compliance because of its simplicity, convenience, effectiveness, etc.

Extensive research with bone histologic changes in patients with osteoporosis has made it apparent that there are two major groups of osteoporotic patients; those with high turnover osteoporosis in whom normal to increased numbers of bone forming and resorbing cells are seen and those with low turnover osteoporosis where the numbers of osteoclasts and osteoblasts are clearly reduced. In patients with low turnover osteoporosis, blocking of osteoclasts will be of little value since there is very little bone resorption taking place and an activation step is generally needed. The present invention effectively treats low turnover and high turnover osteoporosis, whereas many treatment regimens, e.g. those disclosed in U.S. Pat. No. 4,761,406, do not.

U.S. Pat. No. 4,761,406 describes studies done in rats, animals which are known to continue to grow throughout their lives, i.e., the rat skeleton is subjected to "modelling" (resorption takes place at one site and formation of bone at another site). The human skeleton, on the other hand, stops growing after puberty and is subjected to remodelling, whereby a number of factors initiate resorption of bone at a particular remodelling site, leading to a resorption cavity which is later refilled by formation of bone at the same site. Osteoporosis is an abnormality of remodelling (and not modelling) in which a negative bone balance results from excessive resorption over formation or normal resorption with decreased formation (imbalance between resorption and formation). The principle of treating osteoporosis rests with the ability of a given substance to influence resorption (as diphosphonates do) or to stimulate formation, depending on the underlying abnormality. Rat data may give information on effects of certain substances on bone growth (modelling) which might not be applicable to osteoporosis, a disease of remodelling. Blocking bone resorption in a growing skeleton will obviously result in an appreciable increase in bone mass as long as bone formation continues. However, these results cannot be necessarily extrapolated to the abnormality or abnormalities prevailing in osteoporosis. It is conceivable that blocking resorption in a remodelling skeleton would eventually, through the known coupling mechanism between resorption and formation, result in a negative effect on formation. The expected and observed positive effects of diphosphonates on osteoporosis should therefore be seen mainly in the high turnover form of osteoporosis where excessive resorption is found with normal formation.

The mechanism by which bone is lost in osteoporotics is believed to involve an imbalance in the process by which the skeleton renews itself. This process has been termed bone remodeling. It occurs in a series of discrete pockets of activity. These pockets appear spontaneously within the bone matrix on a given bone surface as a site of bone resorption. Osteoclasts (bone dissolving or resorbing cells) are responsible for the resorption of a portion of bone of generally constant dimension. This resorption process is followed by the appearance of osteoblasts (bone forming cells) which then refill with new bone the cavity left by the osteoclasts. In a healthy adult subject, the rate at which osteoclasts and osteoblasts are formed is such that bone formation and bone resorption are in balance. However, in osteoporotics, an imbalance in the bone remodeling process develops which results in bone being lost at a rate faster than it is being made. Although this imbalance occurs to some extent in most individuals as they age, it is much more severe and occurs at a younger age in osteoporotics.

The development of osteoporosis includes two main components, the maximum amount of bone accrued, sometimes referred to as peak bone mass, and the subsequent loss of such bone. Peak bone mass is largely determined by the genetic background of the individual involved, although other factors, such as nutrition in childhood and physical activity, may also be important. The treatment for osteoporosis is generally aimed at preventing bone loss. Only minor amounts of bone mass are lost in women until stoppage of the ovarian function, which occurs during the menopause, and there is then a pronounced loss from all skeletal sites. The rate of bone mass loss generally slows in time, but continues intermittently into old age. The decrease in the bone density associated with osteoporosis is reflected by a continuous increase in the risk of fracture at sites wherein trabecular bone predominates. Thus, for instance, falls by individuals having an osteoporotic condition often result in fracture in the hip or wrist.

EXAMPLE 1

Series I of experiments:

This series of experiments was performed in 225 rats of the same age. 105 rats were ovariectomized. Old rats (approx. 1 year) were used because osteoporosis following ovariectomy is closer to the situation in humans (postmenopausal osteoporosis) if old rats are used. Additionally, the same number of rats were sham operated (same procedure with anaesthesia, opening of the abdomen etc. but without taking away the ovaries). The ovariectomized and the sham operated rats were killed 18 weeks after the surgical procedure. Femurs of all animals were isolated. X-ray density of the distal metaphysis of the right femurs was measured. The results of such a density analysis correlate very well with those of other methods for the determination of bone loss (ash weight, histomorphometric analysis etc.; Bauss F., Minne H. W., Sterz H., Weng U., Wesch H., and Ziegler R.: Comparative bone analysis via inflammation-mediated osteopenia (IMO) in the rat. Clacif. Tissue Int. 37, 539–546, 1985). Additionally, the femurs of 15 rats not ovariectomized or sham operated were analyzed at the time point of the surgical procedures (ovariectomy or sham operation; group 0). The 210 ovariectomized and sham operated rats were divided into 14 groups of 15 animals each. Different treatments were applied to these groups during the 18 weeks of the experiment. In each instance, the rats were administered sodium salt of BM 21.0955 in the indicated amount (calculated as free acid) in physiological saline solvent, except for Group 1, in which only the solvent was administered. The 7 groups with ovariectomized rats are called groups 1 to 7. The 7 groups of sham operated rats are called groups 8 to 14.

| TREATMENT | |
| --- | --- |
| Group 0 | animals killed at the beginning of the study in order to determine baseline bone density; |
| Group 1 | solvent of BM 21.0955 without active drug; daily s.c. (subcutaneous) administration |
| Group 2 | 0.0001 mg/kg BM 21.0955 daily s.c. |
| Group 3 | 0.0003 mg/kg BM 21.0955 daily s.c. |
| Group 4 | 0.001 mg/kg BM 21.0955 daily s.c. |
| Group 5 | 0.003 mg/kg BM 21.0955 daily s.c. |
| Group 6 | 0.01 mg/kg BM 21.0955 daily s.c. |
| Group 7 | 0.03 mg/kg BM 21.0955 daily s.c. |
| Group 8 | same treatment as group 1 |
| Group 9 | same treatment as group 2 |
| Group 10 | same treatment as group 3 |
| Group 11 | same treatment as group 4 |
| Group 12 | same treatment as group 5 |
| Group 13 | same treatment as group 6 |
| Group 14 | same treatment as group 7 |

That means that there are 7 pairs of ovariectomized or sham operated rats with the same treatment (1 and 8; 2 and 9; 3 and 10 etc.).

RESULTS

Results are shown in FIG. 1. The x-ray densities (pixels in FIG. 1) are a measure of bone density of the femurs of group 0 (baseline in FIG. 1) and all the sham operated animals do not show statistically significant differences. In contrast, the groups 1, 2 and 3 show significantly lower bone density than the corresponding groups 8, 9 and 10 (U-test; $p < 0.05$). This demonstrates bone loss due to ovariectomy (comparison of groups 1 and 8). Additionally, comparison of groups 9 and 2; and 10 and 3, respectively, shows that daily administration of 0.0001 mg/kg and 0.0003 mg/kg BM 21.0955, respectively, cannot totally prevent bone loss. In contrast, there are no significant differences between groups 11 and 4; 12 and 5; 13 and 6; and 14 and 7, respectively. This shows that daily administration of 0,001 mg/kg, 0.003 mg/kg, 0.01 mg/kg and 0.03 mg/kg, respectively, totally prevents bone loss. The lowest dose preventing bone loss was 0.001 mg/kg BM 21.0955 daily s.c. Total dose administered in this group (group 4) was $18 \times 7 \times 0.001$ mg/kg $= 0.126$ mg/kg.

Although no direct clinical testing was performed on humans, it is generally recognized that use of old rats enables the best predictive system known in the art for estimating the efficacy of osteoporosis treatment, short of clinical testing.

EXAMPLE 2:

These experiments were performed with 165 old rats.

EXPERIMENTAL PROCEDURE 75 rats were ovariectomized, 75 further animals were sham operated. Again the animals were divided into groups of 15 animals each. Groups B, C, D, E, F are the ovariectomized rates, groups BS, CS, DS, ES, FS are the sham operated animals. Group A are animals without surgical procedure and without treatment. The femurs of these animals were analyzed at the beginning of the 18 weeks treatment of the other groups. In each instance, the rats were administered sodium salt of BM 21.0955 in the indicated amount (calculated as free acid) in physiological saline solvent, except for Group B, in which only the solvent was administered. Treatment schedules for the 18 weeks treatment period were as follow:

| Treatment | |
| --- | --- |
| Group A | animals killed at the beginning of the study in order to determine baseline bone density; |
| Group B | Solvent of BM 21.0955 |
| Group C | 0 001 mg/kg BM 21.0955 daily s.c.; total dose: 0.126 mg/kg |
| Group D | 2 weeks daily 0.003 mg/kg s.c.; 4 weeks off; 2 weeks daily 0.003 mg/kg s.c.; 4 weeks off; 2 weeks daily 0.003 mg/kg s.c.; 4 weeks off; total dose: 0.126 mg/kg |
| Group E | 2 weeks every second day 0.006 mg/kg s.c.; 4 weeks off; 2 weeks every second day 0.006 mg/kg s.c.; 4 weeks off; 2 weeks every second day 0.006 mg/kg s.c.; 4 weeks off; total dose: 0.126 mg/kg |
| Group F | Two injections of 0.021 mg/kg each with an interval of 7 days between these two injections; 4 weeks off two injections of 0.021 mg/kg each with an interval of 7 days; 4 weeks off; two injections of 0.021 mg/kg each with an interval of 7 days; 4 weeks off; total dose: 0.126 mg/kg |

The dose regimens of groups D, E and F (respectively, DS, ES and FS) are illustrated in FIG. 2.

As in the first series of experiments, after the 18 weeks of treatment period, x-ray analysis of the right femurs were performed.

RESULTS

Figure 3:
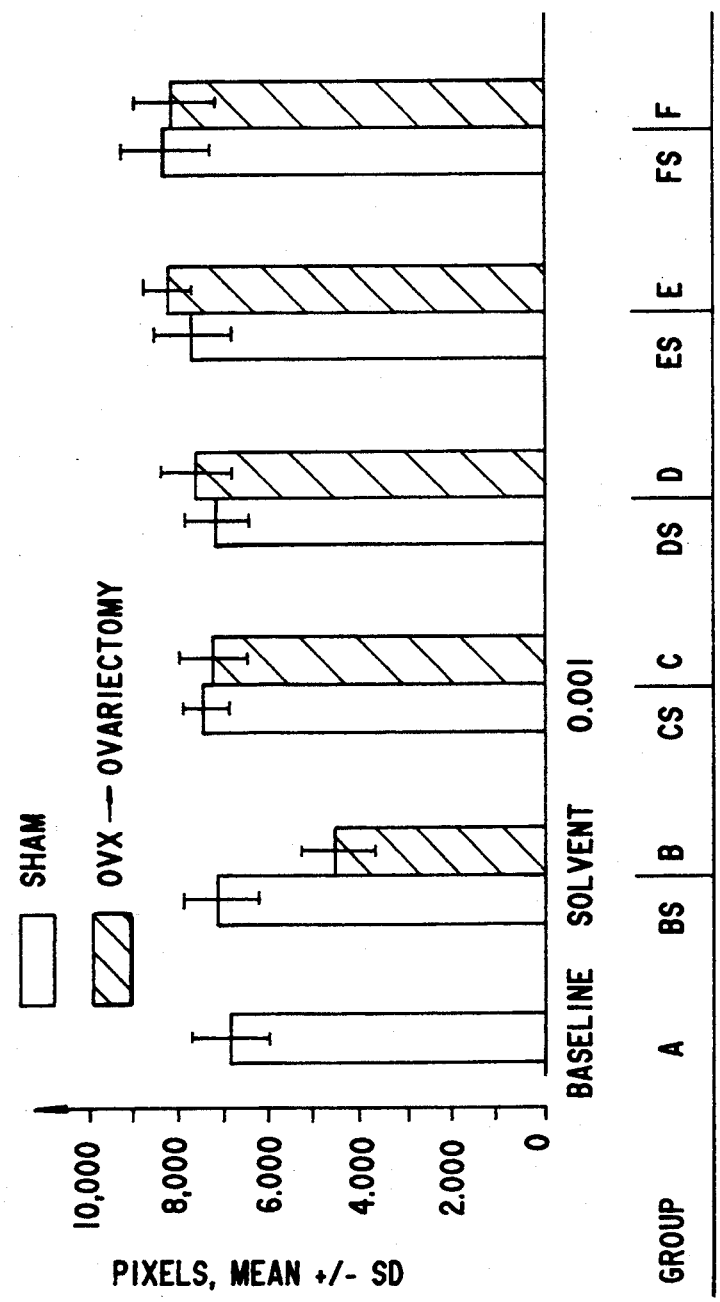
FIG. 3 is a plot of x-ray densities from tests conducted in Example 2.

Results are shown in FIG. 3. Comparison of group A (x-ray density in rats before the 18 weeks treatment period) with BS, CS, DS, ES and FS shows again that there was no bone loss in all sham operated animals. As in series I, there was a significant loss of bone in the ovariectomized animals treated with solvent (group B).

Bone loss was again totally inhibited by daily injections of 0.001 mg/kg BM 21.0955 s.c. (group C). Interval therapy with 2 weeks daily injections and 4 weeks off (groups DS and D) also prevented bone loss. Surprisingly, injections every second day for two weeks, with 4 week rest periods (groups ES and E) and injections every seventh day for two weeks, with 4 week rest periods (groups FS and F) also inhibited bone loss totally.

Polyphosphonates have been given subcutaneously in experiments described herein. In a different series of experiments, it was found that in principle the same results are obtained if the compound is administered orally. Of course, due to the low bioavailability (approx. 1-3%) when administering orally, higher doses have to be taken.

All known bone resorption inhibiting polyphosphonate compounds operate by similar mechanisms. Accordingly, it is clear that the favorable properties achieved according to the treatment regimen of the present invention with any particular polyphosphonate would be similarly obtained with any of the entire class of bone resorption inhibiting polyphosphonate compounds.

Owing to the new treatment schedule according to the present invention, during a drug-on interval, the patient only has to take the drug for example once a week. This can increase patients' compliance (treatment of osteoporosis is typically a chronic treatment). Because bisphosphonates have to be taken at least 2 hours after a meal and 1 hour before a meal (if they are taken with a meal absorption is very low), especially for old patients, correct intake every day is difficult. It is easier to concentrate on the correct drug intake for example only once a week. Additionally, bisphosphonates can cause intestinal discomfort. It is important to have these problems as rare as possible.

The new treatment schedule according to the present invention opens the possibility of chronic osteoporosis therapy by a parenteral route. Whereas daily injections in the drug interval are in general not acceptable (treatment of osteoporosis is usually performed at home and not in the hospital), in contrast, one injection a week (or perhaps even rarer) is much more practical.

Parenteral therapy has advantages compared to oral therapy:

a) Due to low oral bioavailability, there is a large interindividual and even intraindividual scatter of the amount of drug absorbed (up to a factor of 2 to 10). This can cause some patients to be overdosed and others to be underdosed. This situation can be dramatically reduced by parenteral application.

b) Parenteral application avoids gastrointestinal side effects.

In summary, by the new treatment schedules according to the present invention, oral and parenteral therapy can be improved.

Although the regimens and kits in accordance with the present invention have been described in connection with preferred embodiments, it will be appreciated by those skilled in the art that additions, modifications, substitutions and deletions not specifically described may be made without departing from the spirit and scope of the invention defined in the appended claims.

We claim:

1. A method for the treatment of osteoporosis in a patient in need of such treatment, while minimizing the occurrence of patient gastrointestinal problems, said method comprising administering to said patient an effective amount of a bone resorption inhibiting polyphosphonate compound, or a physiologically acceptable salt or ester thereof, wherein the polyphosphonate compound is administered according to a schedule comprising at least two cycles, each said cycle comprising:

(a) an inhibiting period of from about 4 to about 90 days, during which the said polyphosphonate is administered intermittently to the patient, said inhibiting period being divided into at least two intermittent cycle drug administration periods of 2 days to about 14 days, with the drug being administered on only one day of each intermittent cycle drug administration period; and, thereafter, (b) a rest period of from about 20 days to about 120 days.

2. A method as recited in claim 1, wherein said bone resorption inhibiting polyphosphonate compound comprises a compound selected from the group consisting of:

1-hydroxyethane-1,1-diphosphonic acid;
4-amino-1-hydroxybutane-1,1-diphosphonic acid;
3-amino-1-hydroxypropane-1,1-diphosphonic acid;
(4-chlorphenyl)thiomethane-1,1-diphosphonic acid;
1-hydroxy-2-(3-pyridyl)ethane-1,1-diphosphonic acid;
1-hydroxy-1-(1-imidazolyl)ethane-1,1-diphosphonic acid;
1,1-dichlormethane-1,1-diphosphonic acid;
cycloheptylaminomethane-1,1-diphosphonic acid;
3-dimethylamino-1-hydroxypropane-1,1-diphosphonic acid;
1-hydroxy3-(1-pyrrolidinyl) propane-1,1-diphosphonic acid;
1-hydroxy-2-(2-pyridyl)ethane-1,1-diphosphonic acid;
1-hydroxy3-(N-methyl-N-pentyl-amino)-propane-1,1diphosphonic acid; and
1-hydroxy3-(1-iminoethyl)aminopropane-1,1-diphosphonic acid;

or a physiologically acceptable salt or ester thereof.

3. A method as recited in claim 1, wherein said bone resorption inhibiting polyphosphonate compound comprises 1-hydroxy-3-(N-methyl-N-pentyl-amino-propane-1,1-diphosphonic acid.

4. A method as recited in claim 1, 2 or 3, wherein the polyphosphonate is administered orally.

5. A method as recited in claim 1, 2 or 3, wherein the polyphosphonate is administered intravenously.

6. A method as recited in claim 1, 2 or 3, wherein the polyphosphonate is administered subcutaneously.

7. A method as recited in claim 1, 2 or 3, wherein the treatment additionally includes an activation period immediately before the first inhibiting period, said activation period consisting of about 1 to about 30 days, during which a bone cell activating amount of a bone cell activating compound is administered to the patient.

8. A method as recited in claim 7, wherein the bone cell activating compound is administered daily during the activation period.

9. A method as recited in claim 1, 2 or 3, wherein the schedule consists essentially of the inhibiting periods and the rest periods, and the schedule is free of the administration of a bone cell activating compound.

10. A method as recited in claim 1, 2 or 3 wherein said schedule comprises 2 or 3 cycles, said inhibiting periods are each about 14 days in duration, said intermittent cycle drug administration periods are about 7 days in duration, and said rest period is about $2\frac{1}{2}$ months in duration.

11. A method as recited in claim 1, 2 or 3, wherein said at least two intermittent cycle drug administration periods are of different numbers of days.

12. A method as recited in claim 1, 2 or 3, wherein said at least two intermittent cycle drug administration periods are of the same number of days.

* * * * *